United States Patent [19]

Pernice et al.

[11] 4,332,783
[45] Jun. 1, 1982

[54] PROCESS FOR IMMUNOLOGIC DETERMINATION TESTS

[75] Inventors: Walter Pernice; Hans-Harald Sedlacek, both of Marburg an der Lahn, Fed. Rep. of Germany

[73] Assignee: Behringwerke Aktiengesellschaft, Marburg an der Lahn, Fed. Rep. of Germany

[21] Appl. No.: 66,793

[22] Filed: Aug. 15, 1979

[30] Foreign Application Priority Data

Aug. 17, 1978 [DE] Fed. Rep. of Germany ....... 2836046

[51] Int. Cl.$^3$ ..................... G01N 33/54; G01N 33/58; G01N 33/60
[52] U.S. Cl. ..................... 424/1; 23/230 B; 424/12; 435/7
[58] Field of Search ............... 424/1, 11.5, 12; 23/230 B; 435/7

[56] References Cited

U.S. PATENT DOCUMENTS

| Re. 29,474 | 11/1977 | Axen et al. | 424/1 |
|---|---|---|---|
| 4,059,685 | 11/1977 | Johnson | 424/12 |
| 4,061,466 | 12/1977 | Sjohölm et al. | 424/1 |
| 4,067,959 | 1/1978 | Bolz | 424/1 |
| 4,069,352 | 1/1978 | Parsons, Jr. | 23/230 B |
| 4,108,972 | 8/1978 | Dreyer | 424/1 |
| 4,143,124 | 3/1979 | Masson et al. | 424/12 |

*Primary Examiner*—Christine M. Nucker
*Attorney, Agent, or Firm*—Curtis, Morris & Safford

[57] ABSTRACT

What is disclosed is a method for the immunological determination of an immuno-complex, comprising an antigen and an antibody, in a liquid containing said immuno-complex, which method comprises (a) incubating said liquid containing said immumo-complex with a first reagent bound to a carrier, said first reagent being specific for an antigenic determinant of the antigen in said immuno-complex and being present in an amount sufficient to fix said immuno-complex;

(b) separating the carrier from said liquid containing said immuno-complex and incubating it in a solution of a second reagent, said second reagent being specific for an antigenic determinant of the antibody in said immuno-complex and being present in an amount sufficient to fix said immuno-complex; and (c) separating the carrier from said solution of the second reagent and determining the amount of bound or unbound second reagent.

10 Claims, No Drawings

PROCESS FOR IMMUNOLOGIC DETERMINATION TESTS

The present invention concerns an immunologic process for the determination in liquids of an immuno-complex formed from antigens and antibodies.

The so called immuno-complexes are antigen-antibody complexes which are formed not only in vivo but also in vitro in the course of many diseases and are found in body fluids. The antigen of an immunocomplex may be one of many substances formed, in most cases, by microorganisms, viruses, bacteria, parasites, protozoa, etc. and are found in the blood circulation system of species of higher order; they may also be constituents of animal tissues or of malignant cells which, as antigens, induce the formation of antibodies. The antibodies so incited by an antigen are specific for this particular antigen. However, the formation of antibodies within the living organism also induces the formation of antigen-antibody complexes which are called immuno-complexes. In vivo, immuno-complexes are capable of fixing complement factors. In general, immuno-complexes are rapidly eliminated from the organism through the reticuloendothelial system. Under certain circumstances, however, immuno-complexes persist within the body and cause chronic immuno-complex diseases. Persistant immuno-complexes normally have a structure in which not all of the immunological bonding sites of the antigen are covered by antibodies.

The detection of immuno-complexes in body-fluids offers valuable data for the diagnosis of diseases which are called immuno-complex diseases. In the case of such diseases, not only the detection of the immuno-complexes themselves, but also the identification of the antigens contained in them is of utmost importance. Thus, there was a need to find a method for detecting the presence of immuno-complexes which at the same time permitted identification of the antigens. Up to now, a process was known which included two steps and comprised first detecting of the immuno-complex and then identifying the antigen.

Now it has been found that the detection of the presence of immuno-complexes and the identification of the antigen can be carried out in a one-step process.

The process can be carried out in two ways:

(1) Specific reagents A (in general antibodies) directed against the antigen of an immuno-complex are fixed on a carrier. This coated carrier material is brought into contact with the liquid to be tested. Then, the carrier so treated is brought into contact with a solution of an optionally labeled reagent B (antibody, complement), directed against the antibody present in the immuno-complex, and eventually that part of reagent B which is fixed on, or dissolved in, the liquid is determined by measuring the labeling substance.

(2) Instead of the antibody directed against the antigen in the immuno-complex, reagents which are specific for the Fc-part of the immuno-complex-bound antibodies may be fixed on a carrier. Such reagents are, for example, anti-Fc-antibodies, anti-immuno-globulin aggregate-antibodies, rheumatic factors and complement factors.

The carrier-bound immuno-complex is then brought into contact with an optionally labeled reagent (antibody) directed against the antigen in the immuno-complex and the measurement is effected as described under 1).

If a labeled reagent B is used, the quantity of the labeling substance determined in each case indicates the quantity of the fixed immuno-complexes. Such a labeling agent may be, for example, a radio-active atom, an enzyme, a coenzyme or a fluorescent group.

Both methods have in common that antigen-specificity is guaranteed by the use of antigen-specific antibodies. For example, for detecting of HBsAg-containing immuno-complexes, anti-HBsAg-antibodies are necessary and for detecting tetanus-toxoid-containing immuno-complexes, anti-tetanus-toxoid-antibodies are required.

As an alternative to the use of labeling reagents, the immuno-complexes fixed on carriers may also be detected by indicator reactions. These may be carried out by measuring the complement fixation reaction or by agglutination of the carrier.

Accordingly, the object of the present invention is an immunological process for determining an immuno-complex in a liquid, which process is characterized by the fact that (a) a reagent A fixed on a carrier and specific for an antigenic determinant of the antigen or of the antibody is incubated with the liquid containing the immuno-complex in a quantity which is sufficient for binding the immuno-complex, (b) after separation of the liquid, the carrier so treated is incubated with a solution of an optionally labeled reagent B which is specific for an antigenic determinant of the antibody or antigen and which is present in an amount sufficient for fixation on the immuno-complex (c) and the immuno-complex is determined by measuring the fixed or free reagent B in the liquid.

Thus, a reagent A reacting with the antigen or a reagent A reacting with the antibody may be fixed onto the carrier. Correspondingly, the reagent B may be specific for the antibody or for the antigen of the immuno-complex.

Furthermore, another object of the invention is a diagnostic agent for the determination of antigen-specific immuno-complexes, which agent is characterized by that it contains, fixed onto a carrier, reagents which are specific for the antigen or the antibody of the immuno-complex.

GENERAL DESCRIPTION OF THE PROCESS

A reagent A which is specific for the antigen present in the immuno-complex or for the activated Fc-part of immuno-complex-bound antibodies is fixed on a solid carrier. Reagents which are specific for the antigen are antibodies or their antigen-binding fragments. Suitable reagents which are specific for the Fc-part of immuno-complex-bound antibodies have been mentioned above. Since in most cases immuno-complexes fix complement factors already in vivo, even anti-complement-antibodies, for example Fc-specific reagents, may be used.

Suitable carriers are, for example, amorphous particles, spheres, platelets, foils or reaction vessels made of inorganic material (for example glass) or of organic material (for example homo- or copolymers of vinyl compounds such as olefins, vinyl acetate, vinyl chloride, vinylidene chloride, tetrafluoroethylene, styrene, acrylic acid or methacrylic acid, polymers of formaldehyde and cyclic acetals, and polycondensation products such as polyesters, polycarbonates or polyamides or cross-linked hydrocarbons and cross-linked proteins), and of particular biological carriers such as cells (for example erythrocytes).

The fixation may be effected adhesively or covalently. For adhesive coating, the carrier is brought into contact with the reagent. For example, the reagent is dissolved in an aqueous solution, preferably in a buffer (for example, a phosphate-buffered isotonic sodium chloride solution, pH 7.2), at a concentration of 10 $\mu$l/ml, and allowed to stand for 1 minute to 5 days, preferably for 24 hours, with the carrier. The excess of reagent is removed by washing, preferably with a buffer suitably containing a detergent, for example phosphate buffered isotonic sodium chloride, pH 7.2—polyoxyethylene-sorbitane monolaurate ("Tween 20"), 0.1% strength.

Covalent linkages of the respective reagents with the different carriers are formed according to processes known in the literature (cf. Orth et al., Angew. Chemie, 1972, 84, pages 319 ff; Silman et al., Annu. Rev. Biochem., 1966, 35, pages 873 ff; Becht et al., J. Immunology, 1968, 101, pages 18 ff; and M. Lynn, "Immobilized Enzymes, Antigens, Antibodies, and Peptides", edited by Weetall, Marcel Dekker, Inc., New York, page 32, 1975).

The determination of the immuno-complexes is then carried out as follows:

The carrier coated with the respective reagent A is incubated for 1 minute to 48 hours, preferably for 10 hours, with the liquid containing the immuno-complexes and suitably washed with a buffer to remove excess serum constituents.

The carrier so treated is then incubated for 1 minute to 48 hours, preferably for 1 hour, with a solution of a preferably labeled reagent B which is specific for the immuno-complex-bound antibody or, correspondingly, for the antigen in the immuno-complex. Reagents B which are specific for the antibody may be microbial protein A, complement, antibodies or antibody fragments which are directed against antigenic determinants of native or denaturated antibodies.

If the immuno-complex has fixed in vivo complement factors, antibodies or antibody-fragments directed against complement factors may also be used as antibody-specific reagents.

Reagents which are specific for the antigen are antigen-specific antibodies or antibody-fragments. Specific antibody preparations are isolated either from the sera of specifically immunized animals or from human sera (for example, anti-desoxyribonucleic acid-antibodies from sera of patients with Lupus erythematodes, anti-hepatitis-B-antibodies from the sera of patients who have overcome hepatitis, or rheumatic factors from the sera of patients with rheumatoid arthritis) (Lit.: Humphrey and White: Immunologie, Thieme Verlag Stuttgart, 1972; Gell, Coombs, Lachmann: Clinical Aspects of Immunology, Blackwell, Oxford, London, Edinburgh, Melbourne, 1975). The optimum dilutions of reagents to be used in the test must not undergo any unspecific linkage with the carrier, i.e. no linkage with the carrier which can be detected without the presence of carrier-bound immuno-complex. These optimal dilutions have to be specially determined by preliminary tests for each charge of reagent. The usual dilutions are in the range, for example, from 1:10 to 1:400. The controls are performed by tests which are carried out as described above, but with sera without immuno-complexes.

The labeling agents for the reagents are, as already mentioned, radioactive and fluorescent substances or enzymes, for example.

The measurement of the labeling agent is carried out by methods known to experts.

The following examples illustrate the invention.

EXAMPLE 1

Use of a carrier-bound reagent A, specific for antigen tetanus toxoid.

Immuno-complexes with tetanus toxoid as the antigen are prepared by mixing tetanus antibodies of human origin with tetanus toxoid.

Preparation of a carrier coated absorptively with antibodies:

100 microliters of a $1.1 \times 10^{-3}\%$ strength solution (weight protein/volume of phosphate-buffered NaCl solution) of an antigen-tetanus immuno-globulin (rabbit) are filled into small polystyrene tubes having a capacity of 400 microliters and stored at 4° C. After 24 hours, the solution is filtered off with suction. The small tubes are then washed three times with each time 400 microliters of a washing solution of phosphate-buffered NaCl solution, pH 7.2, containing 0.1% (g/v) of "Tween 20").

1. Incubation:

The small tubes coated with the anti-tetanus toxoid are filled with 0.1 ml of the solution prepared as described above and containing the immuno-complex, diluted in a ratio of 1:4 with phosphate-buffered NaCl solution containing 5% of bovine serum albumin and allowed to stand for 10 hours at 21° C. The solution is then filtered off with suction and washed as described for the coating of the carrier.

2. Incubation:

Then, 0.1 ml of a rabbit-anti-human-gammaglobulin, labeled with peroxidase according to the process of Nakane and Kawaoe, J. Histochem. Cytochem., 1972, 22, 1084) in a dilution of 1:50 with phosphate-buffered NaCl solution, containing 5% of bovine serum albumin, is filled into the small tubes and after 1 hour (21° C.) washed as described for the coating.

3. Measurement of the labeling:

0.1 ml of a freshly prepared 0.1% strength o-phenylene-diamine HCl solution in citrate-phosphate buffer (5 ml 0.1 M citric acid + 5 ml 0.2 M Na$_2$HPO$_4$), combined with 0.1 ml of a 1% (v/v) H$_2$O$_2$ solution, was introduced into the small tubes by means of a pipet. After a reaction time of 30 to 60 minutes in the dark, the reaction is stopped with 0.1 ml of a 2 N H$_2$SO$_4$ solution and the extinction is measured with the aid of a Beckmann photometer.

|  | Milli-extinction |
|---|---|
| Immuno-complexes containing tetanus toxoid |  |
| with slight excess of antigen | 2133 |
| with extremely high excess of antigen | 635 |
| Controls |  |
| Pure tetanus toxoid without immuno-complexes | 310 |
| Pure tetanus immuno-serum without immuno-complexes | 831 |

Immuno-complexes can be detected depending on of their composition (ratio of antigen/antibody), and can be detected particularly well with a slight excess of antigens.

EXAMPLE 2

Use of carrier bound reagents A specific for the antigen HBsAg.

Sera of patients with immuno-complexes containing HBsAg and 60 normal sera were tested.

Preparation of the carrier coated absorptively with antibodies:

100 microliters of a $1.1 \times 10^{-3}\%$ strength solution (weight protein/volume, phosphate-buffered NaCl solution) of an antihepatitis-immunoglobulin (rabbit) are filled into small polystyrene tubes having a capacity of 400 microliters. After 24 hours (4° C.) the solution is filtered off with suction and washed three times with 400 microliter portions of a phosphate-buffered NaCl solution, pH 7.2, containing 0.1% (g/v) of "Tween 20".

1. Incubation:

0.1 ml of the immuno-complex containing solution, diluted in a ratio of 1:4 with a phosphate-buffered NaCl solution containing 5% of bovine serum albumin, are filled into the small tubes coated with the rabbit-anti-hepatitis-hyperimmunoglobulin and allowed to stand for 10 hours at 21° C.

The solution is then filtered off with suction and washed as described for the coating of the carrier.

2. Incubation:

Subsequently, 0.1 ml of a rabbit-antihuman gamma-globulin, labeled according to the process described by Nakane and Kawaoe (J. Histochem.Cytochem., 1974, 22, 1084), in a dilution of 1:50 with a phosphate-buffered NaCl solution, containing 5% of bovine serum albumin, is filled into the small tubes and, after 1 hour (21° C.), washed as described for the coating of the carrier.

3. Measurement of the labeling as described in Example 1.

The results are shown in the following Table.

| Serum No. | Diagnosis | Immuno-complex (milli-extinction) HBsAG detected according to Example 2 |
|---|---|---|
| 1 | Hepatitis B | 301 |
| 2 | Hepatitis B | 1107 |
| 3 | Hepatitis B | 1129 |
| 4 | Chron. aggr. Hepatitis B | 1321 |
| 5-65 | 60 Normal sera | 200 |

In the sera of patients with hepatitis, antigen-specific immuno-complexes could clearly be detected.

EXAMPLE 3

Use of polymethyl-methacrylate foil with active azide groups. Coating of the foil:

Equally sized pieces of polymethylmethacrylate having active azide groups, prepared according to the process described by M. Lynn, "Immobilized Enzymes, Antigens, Antibodies and Peptides", edited by Howard H. Weetall, Marcel Dekker, Inc., New York, 1975, page 32), are incubated with a 0.1% strength solution of horse-anti-tetanus toxoid-immunoglobulin in phosphate buffered isotonic sodium chloride solution of pH 7.2 and are washed three times with such a solution to remove excess antibodies.

1. Incubation:

The foil coated with horse-antitoxoid is incubated for 10 hours with the test sample containing the immuno-complexes (immuno-complexes with tetanus toxoid as the antigen as in Example 1) and diluted in a ratio of 1:4 with a solution of albumin in phosphate buffered isotonic sodium chloride of 5% strength. The foil is then washed three times with a washing solution as described in Example 1.

2. Incubation:

Subsequently, the foil is incubated for 1 hour (21° C.) with peroxidase-labeled rabbit-anti-human-gamma-globulin, diluted in a ratio of 1:50 in phosphate buffered isotonic sodium chloride-bovine serum albumin (cf. Example 1), washed three times with a washing solution (as described above) and the labeling on the foil is measured as described in Example 1.

| Results: | Tetanus toxoid without immuno-complexes | Tetanus toxoid containing immuno-complexes with slight excess of antigen | Tetanus-immuno-serum without immuno-complexes |
|---|---|---|---|
| Extinction at 420 nm | 208 | 803 | 245 |

Immuno-complexes which were antigen-specific for the serum and tetanus toxoid without immuno-complexes could be clearly detected in the immuno-complex-containing sample prepared as described in Example 1.

EXAMPLE 4

Use of polymethylmethacrylate foil with active azide groups for the covalent linkage of F(ab)$_2$ fragments:

Coating of the foil:

Polymethylmethacrylate foil pieces of equal size (cf. Example 3) are incubated for 24 hours at 21° C. with a 0.1% strength solution of an anti-tetanus toxoid F(ab)$_2$ preparation (horse) in phosphate buffered isotonic sodium chloride, pH 7.2 [prepared according to process described by Visonoff, A. et al., Arch.Biochem. Biophys. 89, 230 (1960)] and washed three times with a washing solution (cf. Example 1) to remove excess reagents.

1. Incubation

The coated foil is incubated for 10 hours with the test sample which contains the immuno-complexes and has been diluted in a ratio of 1:4 in phosphate buffered isotonic sodium chloride solution, pH 7.2, and bovine serum albumin, 5%, and subsequently washed three times with washing solution.

2. Incubation

The foil is subsequently incubated for 2 hours in peroxidase-labeled (cf. Example 1) anti-human IgG (rabbit), diluted in a ratio of 1.50 with phosphate buffered isotonic sodium chloride solution, pH 7.2, and bovine serum albumin 5%, and then washed three times with washing solution (cf. Example 1).

The labeling on the foil is measured by incubating the foil pieces so prepared for 30–60 minutes in 0.5 ml of a substrate solution (o-phenylene-diamine.HCl-solution, cf. Example 1) and then measuring the extinction of the solution at 490 nm).

| Results: | | |
|---|---|---|
| Tetanus toxoid without immuno-complexes | Tetanus hyperimmune serum with immuno-complexes | Tetanus-hyper-immune serum without immuno-complexes |
| 95 | 495 | 100 |

As compared with the controls without immuno-complexes, the sample with immuno-complexes shows distinctly increased extinction values.

EXAMPLE 5

Use of carrier-bound $Cl_q$ as the reagent, specific for the antibody:

Preparation of the coated carrier:

100 microliters of human $Cl_q$ (purified from human serum according to Haupt, H. and Heimburger, N., Zeitschrift für physiol. Chem., 1972, 535, 1125), 6.1% strength, diluted in phosphate buffered isotonic sodium chloride solution, are filled in small polystyrene tubes having a capacity of 400 microliters and allowed to stand for 24 hours at 4° C. The little polystyrene tubes are then washed thrice with phosphate buffered isotonic sodium chloride solution containing 0.1% of "Tween 20".

1. Incubation

A test sample containing one of the HBsAg immuno-complexes (Hepatitis B associated antigen), diluted in a ratio of 1:4 with phosphate buffered isotonic sodium chloride solution, is filled into the little tubes so treated and incubated for 10 hours at 4° C.

2. Incubation

The little tubes are incubated for 1 hour at 4° C. with 0.11 ml of a rabbit-anti-HBsAg-immunoglobulin, dilluted in a ratio of 1:150 in phosphate buffered isotonic sodium chloride solution containing 5% of bovine albumin, and which has been labeled with peroxidase according to Nakane and Kawaoe (cf. Example 1). The labeling is measured as described in Example 1.

| | Results: | |
|---|---|---|
| Number | Diagnosis | Extinction at 490 nm |
| 1 | Hepatitis (serum without immuno-complexes) | 317 |
| 2 | Hepatitis (serum with immuno-complexes) | 857 |
| 32 | Condition after hepatitis (serum without immuno-complexes) | 317 |

With patient No. 2, the antigen-specific immuno-complex showed distinctly increased values (factor 2.7) as compared to the control values.

EXAMPLE 6

Use of carrier-bound anti-$Cl_q$ as the reagent, "specific" for the antibody.

0.1 ml of an anti-Clq-immunoglobulin (rabbit), dilluted to 0.1% in phosphate buffered isotonic sodium chloride solution, is filled in little polystyrene tubes having a capacity of 400 microliters and allowed to stand for 24 hours at room temperature. The little tubes are then washed three times with washing solution (see above). The first and second incubation and the measurement of the labelling are carried out as described in Example 5.

| | Results: | |
|---|---|---|
| Number | Diagnosis | Extinction at 490 nm |
| 1 | Hepatitis (serum without immuno-complex) | 1 |
| 2 | Hepatitis (serum with immuno-complex) | 33 |
| 3 | Condition after hepatitis (serum without immuno-complexes) | 0 |

The results show clearly increased values in patient No. 2 (factor 33) as compared to the control values.

EXAMPLE 7

Use of carrier-bound anti-human-Fc-antibody as the reagent.

0.1 ml of an anti-human-Fc-immunoglobulin (sheep), diluted to 0.1% in phosphate buffered isotonic sodium chloride solution, is filled into little polystrene tubes having a capacity of 400 microliters and allowed to stand for 24 hours at room temperature. They are then washed three times with washing solution (see above). The first and second incubation and the measurement of the labeling are carried out as described in Example 5.

| | Results: | |
|---|---|---|
| Number | Diagnosis | Extinction at 490 nm |
| 1 | Hepatitis (serum without immuno-complex) | 82 |
| 2 | Hepatitis (serum with immuno-complex) | 290 |
| 3 | Condition after hepatitis (serum without immuno-complexes) | 96 |

The results show clearly increased values in patient serum No. 2 with immuno-complexes as compared with the

EXAMPLE 8

Tanned erythrocytes which had been stabilized according to the process of Becht [J. Immunol. 101, 18 (1968)] with sulfosalicylic acid, in a dilution of 2% strength in phosphate buffered isotonic sodium chloride solution, are incubated for 24 hours at 4° C., while shaking, with anti-tetanus toxoid-immunoglobulin (horse) in a strength of 0.01%, subsequently washed three times in phosphate buffered isotonic sodium chloride solution, containing 0.1% of "Tween 20", and adjusted to a cell suspension of 1% strength.

1. Incubation 50 microliters of the suspension of erythrocytes are incubated for 2 hours, while shaking, with 50 microliters of tetanus toxoid-human-antitoxoid-IC-containing test samples, diluted in a ratio of 1:4 with phosphate buffered isotonic sodium chloride solution, pH 7.2, and subsequently washed three times with washing solution.

2. Incubation

The cell sediment is diluted in a ratio of 1:16 with 100 microliters of freshly isolated quinea pig serum, incubated, while shaking, for 30 minutes at room temperature and then allowed to stand (10 min/21° C.) until the erythrocytes have settled at the bottom of the little tubes.

3. Measurement of the consumption of complement

Fresh sheep erythrocytes are washed three times with phosphate buffered isotonic sodium chloride solution. 1 ml of cell sediment is suspended with 0.5 ml of 1% strength CrCl₃-solution in PBS and mixed with 0.5 ml of human-immunoglobulin having a strength of 10%, washed three times after 4 minutes with PBS and adjusted to a 1% strength cell suspension. Equal volumes of the 1% strength cell suspension and of a rabbit-antihuman-IgG-serum, 1% strength in phosphate buffered isotonic sodium chloride solution, are combined and incubated for 45 minutes at room temperature, while shaking.

50 microliters of the cell suspension so obtained are allowed to stand for 30 minutes at 37° C. with 50 microliters of the supernatant obtained after the second incubation. The extinction of the cell-free supernatant is measured at 546 nm with a Beckmann-photometer. Low extinction values indicate a high consumption of complement in the second incubation step and therewith a high content of immuno-complexes in the samples; high values indicate that the test samples contain only a few immuno-complexes.

| | Results: | | | |
|---|---|---|---|---|
| | Tetanus toxoid-antibody-IC with extreme antigen excess | Tetanus toxoid-antibody-IC with slight antigen excess | Tetanus toxoid-antibody-IC with excess of antibodies | Antibodies without immuno-complex |
| Serum dilution 1:4 Extinction 546 nm | 295 | 99 | 215 | 165 |

The results clearly show the antigen-specific detection of immuno-complexes, especially in the case of immuno-complexes with a slight excess of antigen.

What is claimed is:

1. A method for the immunological determination of a immuno-complex, comprising an antigen and an antibody, in a liquid containing said immuno-complex, which method comprises
    (a) incubating said liquid containing said immuno-complex with a first reagent bound to a carrier, said first reagent being specific for an antigenic determinant of the antigen in said immuno-complex and being present in amount sufficient to fix said immuno-complex;
    (b) separating the carrier from said liquid containing said immuno-complex and incubating it in a solution of a second reagent, said second reagent being specific for an antigenic determinant of the antibody in said immuno-complex and being present in an amount sufficient to fix said immuno-complex; and
    (c) separating the carrier from said solution of the second reagent and determining the amount of bound or unbound second reagent.

2. A method as in claim 1 wherein said carrier is a biological particle or a shaped organic or inorganic body.

3. A method as in claim 1 wherein said first reagent is bound covalently or adsorptively to said carrier.

4. A method as in claim 1 wherein said second reagent is labelled.

5. A method as in claim 1 wherein at least one of said first or second reagents is an antibody fragment.

6. A method as in claim 1 wherein said second reagent is protein A from Staphylococcus aureus.

7. A method as in claim 1 wherein said second reagent is a complement factor.

8. A method as in claim 1 wherein said second reagent is an antibody or antibody fragment directed against the complement.

9. A method as in claim 1 wherein said second reagent is an antibody against the Fc-fragment of immunoglobulin or against immunoglobulin aggregates, or against a rheumatic factor.

10. A method as in claim 1 wherein said second reagent is labelled with a radioactive substance, an enzyme, a co-enzyme, or a fluorescent substance.

* * * * *